(12) United States Patent
McMahon et al.

(10) Patent No.: US 7,882,928 B2
(45) Date of Patent: Feb. 8, 2011

(54) ACOUSTIC MEASUREMENT TIP

(75) Inventors: Michael T. McMahon, Syracuse, NY (US); Steven R. Slawson, Camillus, NY (US); David C. Woods, Memphis, NY (US); Andrew J. Kugler, Albany, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 198 days.

(21) Appl. No.: 12/146,674

(22) Filed: Jun. 26, 2008

(65) Prior Publication Data
US 2009/0321177 A1 Dec. 31, 2009

(51) Int. Cl.
*A61B 7/02* (2006.01)

(52) U.S. Cl. ...................... 181/135; 600/559

(58) Field of Classification Search ............... 181/135; 600/559; D24/173
See application file for complete search history.

(56) References Cited

U.S. PATENT DOCUMENTS

| | | | |
|---|---|---|---|
| 3,105,876 A | 10/1963 | Mullin et al. | |
| 3,513,269 A | 5/1970 | Wilson | |
| 3,882,848 A | 5/1975 | Klar et al. | |
| 3,934,100 A | 1/1976 | Harada | |
| 4,002,161 A | 1/1977 | Klar et al. | |
| 4,009,707 A | 3/1977 | Ward | |
| 4,057,051 A | 11/1977 | Kerouac | |
| 4,122,841 A | 10/1978 | Rock et al. | |
| 4,237,905 A | 12/1980 | Keller et al. | |
| 4,441,576 A | 4/1984 | Allen | |
| 4,548,082 A | 10/1985 | Engebretson et al. | |
| 4,841,986 A | 6/1989 | Marchbanks | |
| D419,675 S | 1/2000 | Garcia | |
| 6,042,266 A | 3/2000 | Cheslock et al. | |
| 6,048,320 A | 4/2000 | Brainard, II | |
| 6,126,614 A | 10/2000 | Jenkins et al. | |
| 6,129,174 A | 10/2000 | Brown et al. | |
| 6,139,507 A | 10/2000 | Jeng | |
| 6,152,596 A | 11/2000 | Fraden | |
| 6,358,216 B1 * | 3/2002 | Kraus et al. | 600/549 |
| 6,702,758 B2 | 3/2004 | Iseberg | |
| 7,079,198 B2 | 7/2006 | Miyazaki et al. | |
| 7,129,632 B2 | 10/2006 | Park et al. | |
| 7,266,208 B2 | 9/2007 | Charvin et al. | |
| 7,354,399 B2 * | 4/2008 | Strom et al. | 600/200 |

(Continued)

OTHER PUBLICATIONS

International Search Report and Written Opinion for PCT/US2009/048749, mailed Feb. 4, 2010 (10 pages).

*Primary Examiner*—Elvin G Enad
*Assistant Examiner*—Forrest M Phillips
(74) *Attorney, Agent, or Firm*—Roger P. Bonenfant

(57) ABSTRACT

A tip for coupling sound between a medical instrument and an ear includes a sealing surface configured to substantially conform the tip to an auditory canal of the ear. The tip includes an acoustic tube acoustically coupled to at least one of the plurality of openings and defining a first acoustic path. The tip also includes a second acoustic path acoustically coupled to at least another one of the plurality of openings in the sealing surface. The acoustic tube of the first acoustic path is configured to substantially acoustically isolate the first acoustic path from the second acoustic path. A tympanometric instrument is configured to use the tip and to provide an acoustic measurement of the ear of a patient.

43 Claims, 10 Drawing Sheets

U.S. PATENT DOCUMENTS

| | | |
|---|---|---|
| 2002/0058881 A1* | 5/2002 | Raviv et al. .................. 600/559 |
| 2003/0081794 A1 | 5/2003 | Fushimi et al. |
| 2004/0019294 A1* | 1/2004 | Stirnemann ................. 600/559 |
| 2004/0071295 A1 | 4/2004 | Wasden et al. |
| 2005/0015018 A1* | 1/2005 | Dolphin et al. ............. 600/559 |
| 2005/0226307 A1* | 10/2005 | Lussier et al. ............... 374/131 |
| 2007/0112279 A1 | 5/2007 | Iseberg et al. |
| 2007/0129632 A1 | 6/2007 | Voie et al. |
| 2007/0161924 A1 | 7/2007 | Dolphin et al. |
| 2008/0013767 A1 | 1/2008 | Olsen et al. |

* cited by examiner

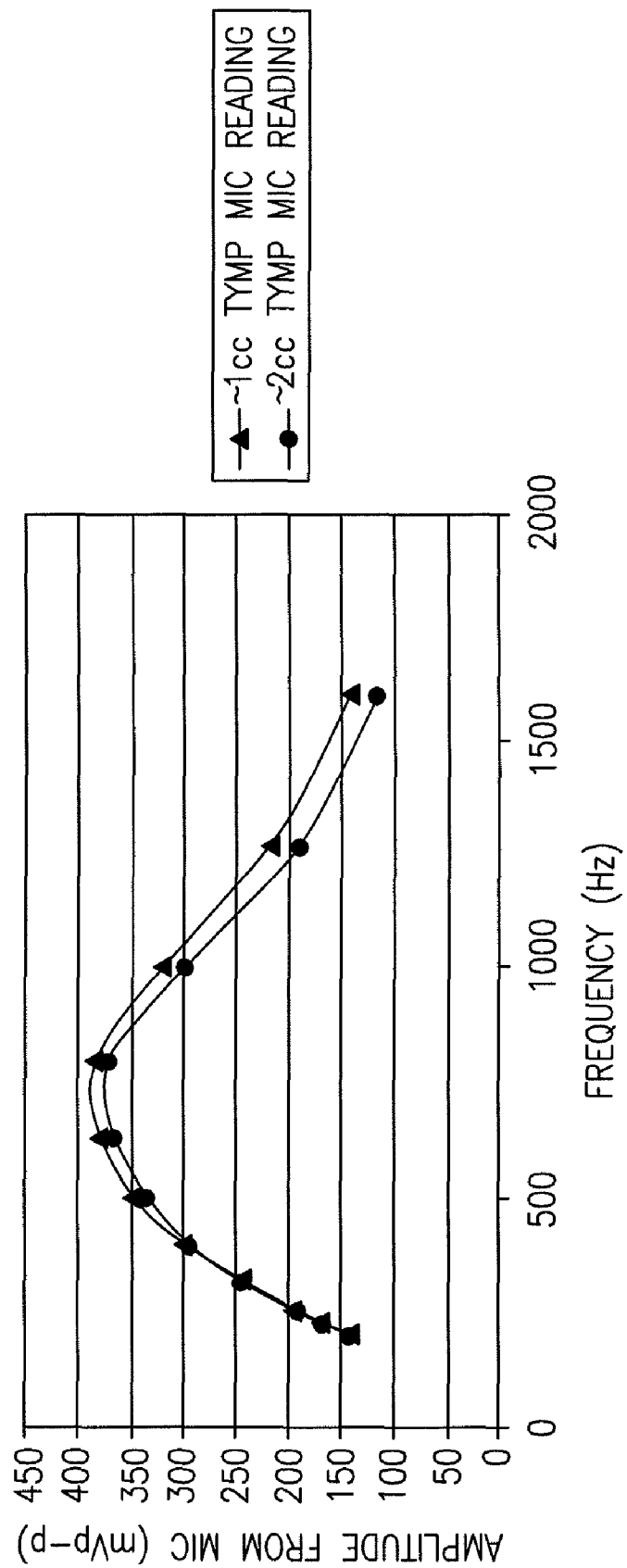

ACOUSTIC MEASUREMENT TIP

FIELD OF THE INVENTION

This invention relates generally to an acoustic tip and more particularly to an acoustic tip for an audiological medical instrument.

BACKGROUND OF THE INVENTION

A "tip" of the prior art includes components used to make an acoustic-mechanical connection with the ear of a patient for medical instruments that can sense and measure physiological parameters of the human ear. A pliable silicone or plastic tip having a flexible surface, such as a flexible seal, can be seated against the outer surface of the auditory canal for acoustic measurements. The tip can provide both an acoustic interface to the auditory canal as well as a pneumatic pressure seal. The properties of the acoustic interface should be compatible with the frequency or tone of test signals being used.

In the field of tympanometry, an example of a field that relates to acoustic measurements of the ear, a medical instrument typically measures the impedance or admittance of the ear canal/tympanic membrane/middle ear system. To make a tympanometric measurement, an audio signal is first transmitted into the auditory canal, generally by an acoustic transmitter, such as a small speaker in the tympanometric instrument while a small microphone in the instrument simultaneously monitors sound in the auditory canal. This process is continued while varying the static pressure inside the ear canal, typically using a pump or similar means. The instrument can thus measure the changing impedance or admittance of the ear system as a function of pressure. The results of such measurements, indicating mobility of the tympanic membrane and ossicular chain, can be helpful to clinicians in assessing and diagnosing various conditions and pathologies of the ear.

By convention and standards, tympanometric measurements have generally been performed at a fixed frequency of about 226 Hz. Various forms of tympanometric instruments and tips have been commonly used. Based on relatively recent research, there is a move in the industry towards using 1,000 Hz as the new standard frequency, especially for infants & patients under 6 months of age.

For prior art devices that currently use a 226 Hz probe tone, a direct conversion or upgrade to a 1000 Hz probe tone can create problems with instrument accuracy.

What is needed, therefore, is an acoustic-mechanical tip for a medical instrument that can provide accurate acoustic-physiological measurements using audio frequencies of 1,000 Hz or greater.

SUMMARY OF THE INVENTION

According to one aspect, a tip is provided for coupling sound between a medical instrument and an ear which includes a sealing surface configured to substantially conform the tip to an auditory canal of the ear. The sealing surface includes a plurality of openings. The tip also includes a first acoustic path having an acoustic tube acoustically coupled to at least one of the plurality of openings, the acoustic tube being disposed within the tip. The tip also includes a second acoustic path acoustically coupled to at least another one of the plurality of openings in the sealing surface, wherein a selected one of the first acoustic path and the second acoustic path is configured for acoustic transmission, and another one of the first acoustic path. The second acoustic path is further configured for acoustic detection, the acoustic tube of the first acoustic path being configured to substantially acoustically isolate the first acoustic path from the second acoustic path.

In one embodiment, the tip includes one or more mechanical attachment members configured to mechanically suspend the acoustic tube within the tip.

In another embodiment, the acoustic tube and the one or more mechanical attachment members include substantially the same material.

In yet another embodiment, the material includes a pliable material.

In yet another embodiment, the pliable material includes a silicone.

In yet another embodiment, the acoustic tube is mechanically suspended substantially on a longitudinal axis of the tip.

In yet another embodiment, the sealing surface includes a diameter larger than an opening to the auditory canal.

In yet another embodiment, the configuration to substantially acoustically isolate the first acoustic path from the second acoustic path substantially suppresses Helmholtz resonance effects at the tip.

In yet another embodiment, the configuration to substantially acoustically isolate the first acoustic path from the second acoustic path reduces noise.

In yet another embodiment, the configuration to substantially acoustically isolate the first acoustic path from the second acoustic path provides artifact rejection.

In yet another embodiment, the at least a selected one of the first acoustic path and the second acoustic path is acoustically coupled to an acoustic detector configured for the acoustic detection.

In yet another embodiment, the acoustic detector includes a microphone.

In yet another embodiment, the acoustic path is configured for acoustic transmission includes at least one speaker.

In yet another embodiment, the tip further includes a plurality of acoustic paths, at least a selected one of the plurality of acoustic paths acoustically coupled to more than one of the plurality of openings.

In yet another embodiment, the acoustic path configured for acoustic transmission operates at one or more selected frequencies over a range of frequency of about 200 Hz to 20 kHz.

In yet another embodiment, the acoustic transmitter operates at about 1,000 Hz.

In yet another embodiment, the tip is a disposable tip.

In yet another embodiment, the tip is configured for single use and wherein at least the sealing surface includes a material designed to deteriorate to discourage reuse.

In yet another embodiment, at least a portion of the tip is configured to deteriorate on exposure to a cleaning chemical.

In yet another embodiment, the medical instrument is a tympanometric instrument.

In yet another embodiment, the tympanometric instrument further includes at least one pump configured to apply a pressure in the auditory canal via the at least one at least one of the plurality of openings in the sealing surface.

In yet another embodiment, the acoustic tube is configured to slidably engage an extension tube disposed within a front end of the medical instrument.

In yet another embodiment, the tip remains substantially free of Helmholtz resonance over a range of slidable mechanical engagement.

According to another aspect, an acoustic measurement apparatus includes a tip having a sealing surface configured to substantially conform the tip to an auditory canal of the ear. The sealing surface includes a plurality of openings. The tip further includes an acoustic tube acoustically coupled to at least one of the plurality of openings defining a first acoustic path, the acoustic tube being disposed within the tip, the tip also includes a second acoustic path acoustically coupled to at least another one of the plurality of openings in the sealing surface. A selected one of the first acoustic path and the second acoustic path is configured as a path for acoustic transmission, and another one of the first acoustic path. The second acoustic path is further configured as a path for acoustic detection, and the acoustic tube of the first acoustic path is configured to substantially acoustically isolate the first acoustic path from the second acoustic path. The acoustic measurement apparatus includes an acoustic measuring device. The acoustic measuring device includes a front end which receives the tip, the front end includes at least two acoustic paths configured to acoustically couple to the first acoustic path and the second acoustic path of the tip. The acoustic measuring device also includes an acoustic transmitter acoustically coupled via the path for acoustic transmission. The acoustic measuring device also includes an acoustic detector coupled via the path for acoustic detection. The acoustic measuring device also includes an electronics package electrically coupled to the acoustic transmitter, the electronics package also being electrically coupled to the acoustic detector. The electronics package includes at least one microcomputer. The at least one microcomputer is configured to run an algorithm for performing an acoustic measurement.

In one embodiment, the tip includes one or more mechanical attachment members configured to mechanically suspend the acoustic tube within the tip.

In another embodiment, the tip, including the acoustic tube and the one or more mechanical attachment members, includes substantially the same material.

In yet another embodiment, the material includes a pliable material.

In yet another embodiment, the pliable material includes a silicone.

In yet another embodiment, the acoustic tube is mechanically suspended substantially on a longitudinal axis of the tip.

In yet another embodiment, the sealing surface includes a diameter larger than an opening to the auditory canal.

In yet another embodiment, the configuration to substantially acoustically isolate the first acoustic path from the second acoustic path substantially suppresses Helmholtz resonance effects at the tip.

In yet another embodiment, the configuration to substantially acoustically isolate the first acoustic path from the second acoustic path reduces noise.

In yet another embodiment, the configuration to substantially acoustically isolate the first acoustic path from the second acoustic path provides artifact rejection.

In yet another embodiment, the acoustic detector includes a microphone.

In yet another embodiment, the acoustic path is configured for acoustic transmission includes at least one speaker.

In yet another embodiment, the tip further includes a plurality of acoustic paths, at least a selected one of the plurality of acoustic paths acoustically coupled to more than one of the plurality of openings.

In yet another embodiment, the acoustic path configured for acoustic transmission operates at one or more selected frequencies over a range of frequency of about 200 Hz to 20 kHz.

In yet another embodiment, the acoustic transmitter operates at about 1,000 Hz.

In yet another embodiment, the tip is a disposable tip.

In yet another embodiment, the tip is configured for single use and wherein at least the sealing surface includes a material designed to deteriorate to discourage reuse.

In yet another embodiment, at least a portion of the tip is configured to deteriorate on exposure to a cleaning chemical.

In yet another embodiment, the medical instrument includes a tympanometric instrument.

In yet another embodiment, the tympanometric instrument further includes at least one pump configured to apply a pressure in the auditory canal via the at least one at least one of the plurality of openings in the sealing surface.

In yet another embodiment, the acoustic tube is configured to slidably engage an extension tube disposed within a front end of the medical instrument.

In yet another embodiment, the front end is configured to mechanically couple with the acoustic tube with a range overlap, wherein once mechanical engagement of the tip creates a substantially air tight seal between the first acoustic path and the second acoustic path of the tip and the front end, the tip remains substantially free of Helmholtz resonance over a range of depths of the overlap.

In yet another embodiment, the front end is configured to mechanically couple to the acoustic tube with a range overlap, wherein once mechanical engagement of the tip creates a substantially air tight seal between the first acoustic path and the second acoustic path of the tip and the front end, the tip remains substantially free of a Helmholtz resonance over a range of depths of the overlap.

In yet another embodiment, the apparatus is a portable instrument that further includes a display communicatively coupled to the microcomputer and configured to display a result of a tympanometric measurement.

In yet another embodiment, the front end further includes a central core having a central core stem section, wherein the central core stem section is configured to slidably engage the acoustic tube in order to complete the first acoustic path.

In yet another embodiment, the central core further includes at least one acoustic channel which is acoustically coupled to the second acoustic path of the tip.

In yet another embodiment, the front end further includes a reinforcing sleeve disposed coaxially over the central core and the reinforcing sleeve is configured to mechanically engage the tip to mechanically mount the tip onto the front end.

In yet another aspect, a method of affixing a tip for the acoustic measurement of an ear to a front end of an acoustic measurement instrument includes the steps of: (a) providing an acoustic tip configured to make a seal with an auditory canal of the ear, the sealing surface includes a plurality of openings, and defining at least a first and a second acoustic path, the first acoustic path of the tip includes an acoustic tube substantially extending substantially to the sealing surface; (b) providing an acoustic instrument front end configured to mate to the tip; and (c) sliding the tip onto the front end to sealingly engage both the acoustic tube of the at least a first acoustic path and the second acoustic path of the tip with at least a first and a second acoustic path of the front end.

In one embodiment, the method further includes the step (d) sliding the tip off of the front end to sealingly disengage both the acoustic tube of the at least a first acoustic path and the second acoustic path of the tip using an ejector device.

BRIEF DESCRIPTION OF THE DRAWINGS

For a further understanding of these and objects of the invention, reference will be made to the following detailed description of the invention which is to be read in connection with the accompanying drawings, where:

FIG. 9B shows a graph of the results of the same laboratory test performed in FIG. 9A using an exemplary tip according the invention;

The drawings are not necessarily to scale, emphasis instead generally being placed upon illustrating the principles of the invention. In the drawings, like numerals are used to indicate like parts throughout the various views.

DETAILED DESCRIPTION

Tympanometry has traditionally been performed at an audio frequency of 226 Hz. As previously noted, it is now believed that more accurate results can be achieved using a higher frequency. The task force in newborn screening (JCIH), for example, has recommended that 1,000 Hz become the new standard frequency for tympanometry. Thus, there is a present trend in the medical sciences, to perform such acoustic measurements of the ear at an audio frequency of 1,000 Hz.

Figure 1:
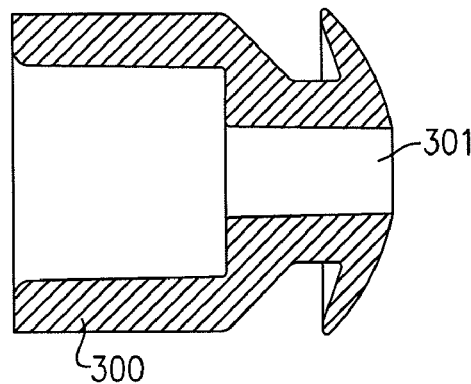
FIG. 1 shows a cutaway side view of a traditional 226 Hz tympanometric instrument in accordance with the prior art.

While testing at higher frequencies with traditional 226 Hz tips and front ends, it has been realized that measurements made at 1,000 Hz were in error. FIG. 1 shows one exemplary tip of the prior art. During development of a 1,000 Hz product, it became clear that using such prior art tips, which function correctly and give good results at 226 Hz, do not work correctly at 1,000 Hz. We believe that the reason prior art tips 300 give erroneous results can be attributed to the 'Helmholtz Resonator' acoustic phenomenon, which begins to take place at the higher frequency. This effect, in which the slug of air residing in the tip's distal bore begins to resonate, reduces the sound pressure immediately in front of the microphone. The microphone thus reports a lower sound level than actually exists in the ear canal and the corresponding measurement, such as an admittance level, is reported in error by the instrument. The Helmholtz acoustic phenomenon is described in more detail in Appendix I. It has subsequently been realized that the tip and mating front end designs can be suitably modified such that the tip itself becomes a functioning part of the acoustical system.

Definition: As used herein, "tip" is defined as a component that can matingly engage the "front end" of an acoustic instrument and to provide a substantially sealed mating interface to a physiological structure, such as the opening to the auditory canal of a human ear. A tip is a removable element generally made from one or more pliable materials. A tip as construed herein is typically manufactured and made available in a number of various sizes. The purpose of providing a range of seal sizes is to provide a substantially optimal seal with an animal or human physiological feature of varying sizes, most commonly the opening to an auditory canal of the human ear. Suitable tip sizes can vary from human to human or from animal to animal, such as by age (e.g. a baby's ear and an adult's ear). Generally what distinguishes the various tip sizes is the size of the sealing surface.

A tip as herein described that provides a mechanical acoustic interface between a medical instrument, such as a tympanometric instrument, and the human ear. The tip is typically associated with and attached to the medical instrument via a medical instrument "front end". As to be construed in herein, the word "tip" does not include the front end or elements of an acoustic instrument or device front end. An instrument or device front end generally includes an assembly of parts, typically including one or more acoustic channels. A user can matingly affix a tip to a front end which conducts acoustic energy to and from the rest of the device such as via discrete metal tubes or other surgical tubes that typically extend to, or into a tip.

The phrase "acoustic tube" as used herein is defined as an integral part of the tip. As an integral part of a tip, when a tip slidingly engages or disengages with a front end of a medical instrument, the acoustic tube always remains with the tip as a part of the tip. While a tip can typically be molded in one piece from a pliable material such as silicone, a tip made from more than one material, such as, for example, including a pliable seal and a less pliable acoustic tube does still fall within the meaning of the term tip as contemplated herein. In other words, while a removable tip is always a one piece component once manufactured, the tip can be manufactured from more than one discrete part and more than one type of material.

While the principles of tympanometry are discussed generally infra, the focus of this description is upon the inventive tip itself. One exemplary prior art 226 Hz tympanometric instrument, generally suitable for use with such a tip as described herein, was previously described in U.S. Pat. No. 4,688,582, Portable Hand-Held Tympanometer, issued Aug. 25, 1987 to Heller, et. al., and assigned to Welch Allyn, Inc., also the assignee of the present invention. The '582 patent is incorporated herein by reference in its entirety.

Figure 2A:
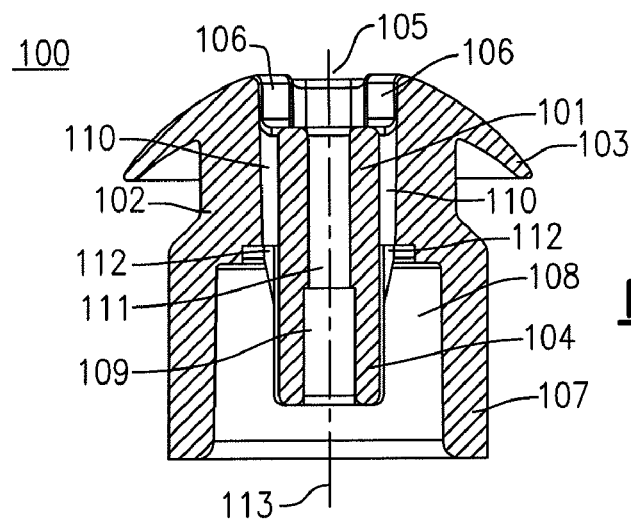
FIG. 2A shows a cutaway side view of one exemplary embodiment of the inventive tip.

FIG. 2A shows a cutaway view of one exemplary embodiment of the inventive tip herein referenced as 100. FIG. 3 illustrates how a sealing surface 103 (typically a curved surface) can provide, for example, a substantially air-tight acoustic seal with the exposed outer surface of the auditory canal of the ear. Although less common, in some embodiments, an especially pliable material can be substantially flat until pressed and conformed to the surface to which the tip is to seal against. A tip 100 can also seal against the inner surfaces of the auditory canal (not shown in FIG. 3). A plurality of openings 106 (FIG. 2A, FIG. 2B end view of tip 100) extending into the distal end of the tip can provide both an acoustic and a pneumatic air pathway for sound generated by a medical instrument, such as a tympanometric instrument, to enter the auditory canal of an ear being tested. In many types of acoustic measurements of the ear, as described in more detail below, there can also be a suction (vacuum) or pressurization of the ear canal as sealed by a sealing surface 103. Air flow for vacuum or pressurization of the ear canal can typically be accomplished, such as with a pump, through openings 106 and air channels 110. For example, a pump can be configured to apply a pressure different from ambient atmospheric pressure in the auditory canal (not shown) via openings 106. Typically by applying a pressure in the auditory canal, we are referring to a pressure that can be varied across a range of pressures from below ambient, through and including ambient, to slightly above ambient pressure. Opening 105, shown substantially in the center of the tip 100 and air channel 111 provides an acoustic air pathway for sound to return to a microphone, or equivalent sound energy measurement transducer or acoustic detector, disposed within an attached medical instrument. Acoustic tube 101, which is mechanically coupled to a sound transducer, such as a microphone, or a microphone tube that can couple to a microphone, represents an advance over the prior art. Section 107 provides a first roughly cylindrical shaped opening 108. Lower microphone tube section 104 also provides a second roughly cylindrical shaped opening 109. Sections 104 and 107 can act as connector receptacles for mechanical attachment to the "front end" of the medical instrument as described further below.

Figure 2B:
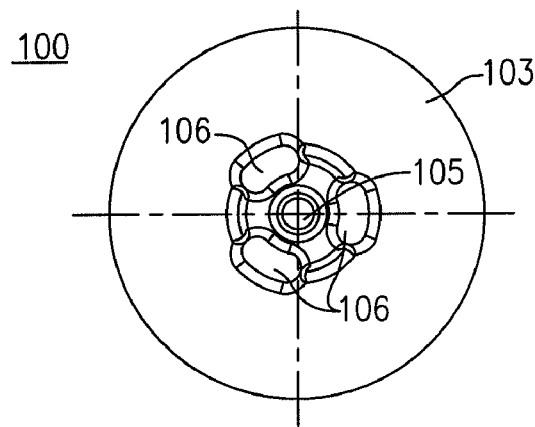
FIG. 2B shows an end view of the tip of FIG. 1A.
Figure 3:
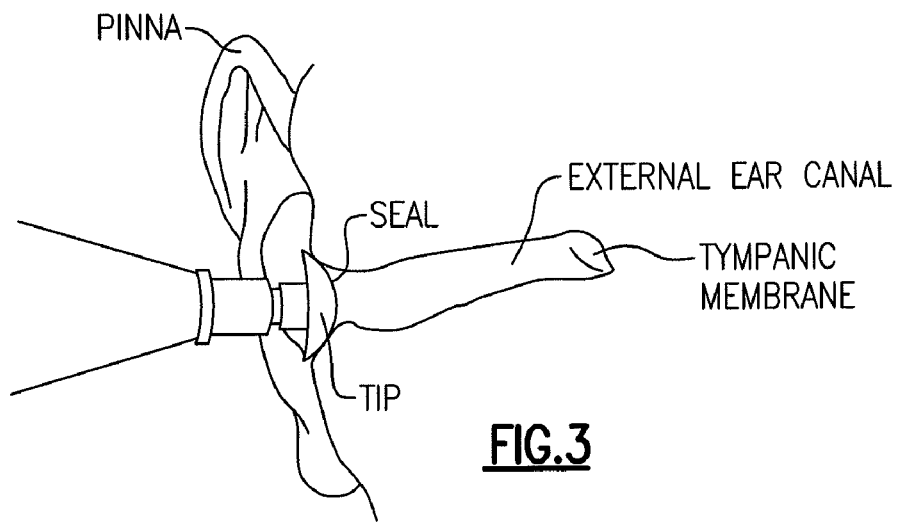
FIG. 3 illustrates the tip seal of FIG. 2A and FIG. 2B as seated and sealed against the outer surface of an auditory canal.

Referring to FIG. 2A and FIG. 2B, tip 100 includes an acoustic tube 101, which can continue as a separate tube extending substantially out to the distal end of tip 100. Acoustic tube 101 can generally be affixed substantially coaxially within a tip 100 by connecting members 112. Note that connecting members 112 (See also FIG. 4B) also allow for sound to pass between roughly cylindrical shaped openings 108 and air channels 110 to openings 106. Also, note that acoustic tube 101 can be mounted within tip 100 at other than the longitudinal axial center of tip 100. For example, an acoustic tube 101 can be present as defined, and largely surrounded by air, except mounted off-center within tip 100 and/or acoustically coupled to an off-center opening 105.

Acoustic tube 101 keeps the microphone channel 109 substantially isolated from any Helmholtz effects that can occur further back in the tip. By adding acoustic tube 101 to the inventive tip, measurement accuracy was restored. Therefore, acoustic tube 101 solves the problem of Helmholtz resonation of a volume of air between a sound sensor disposed in the medical instrument and the interface between the tip and the auditory canal.

In addition to suppression of Helmholtz resonance, acoustic tube 101 can also help to minimize undesirable noise interference and provide artifact rejection. Thus, separation of the acoustic paths can reduce the amount of noise that interferes with the returning signal. When the acoustic and pneumatic paths merge before the distal end of the tip, any noise generated by the pneumatic system or acoustic transmitter can immediately travel back to the acoustic detector, before any filtering caused by the tip volume or volume under test, i.e. an ear canal, can occur. The signal to noise ratio is also reduced. By maintaining separation, such as by use of an acoustic tube 101, any generated noise first fills the volumes in both the front end and the tip before entering the detection channel and the noise fills the volume under test at the same time as it travels back to the detection device. Filling these volumes while maintaining separation reduces the intensity of the noise and provides some filtering.

Various laboratory testing, some of which is described in more detail below, has indicated that a tip having substantially the structure shown in FIGS. 2A and 2B, can be used for acoustic measurements from about 200 Hz to 8 kHz. It is contemplated that such a tip can be used to perform substantially accurate audio measurements all of the way to the end of the audible range of the audio spectrum in the vicinity of 20 kHz.

While all tips 100 as contemplated herein can be removable, some can be simply replaceable, such as to remove for cleaning or to change tip sizes. In other embodiments, tips 100 can be manufactured from more economical materials, such as for example PVC plastics, can be considered disposable. One of the advantages of disposable tips is the far reduced risk of cross contamination from patient to patient. To encourage hygienic practice where the application calls for disposable (as opposed to simply removable) tips, a relatively fast degrading or deteriorating plastic such as a fast degrading PVC can be used. For example, once removed from a package and used one time, an application of a cleaning chemical, such as a disinfecting agent, could accelerate the degradation process. At least some portion of a so designed tip would begin to deteriorate, especially in the thinner seal area after exposure to cleaning chemicals, rendering it useless and thus intentionally and by design discouraging reuse.

Figure 4A:
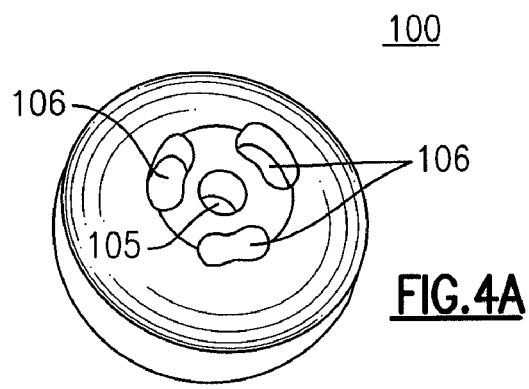
FIG. 4A shows a perspective distal view of an exemplary inventive tip.
Figure 4B:
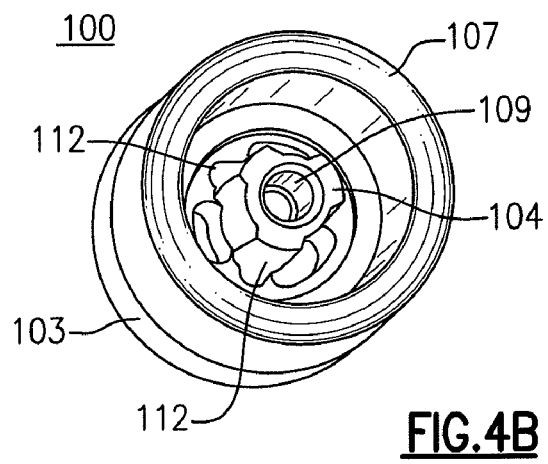
FIG. 4B shows a perspective proximal view of an exemplary inventive tip.

FIG. 4A and FIG. 4B show respectively a front and rear perspective view of tip 100. Tip 100 can generally be manufactured from a pliable material, such as silicone, so that the sealing surface 103 can more easily conform, for example, to the surface of an individual's ear. Tip 100 can be made by any suitable manufacturing process such as, for example, by injection molding.

Figure 5A:
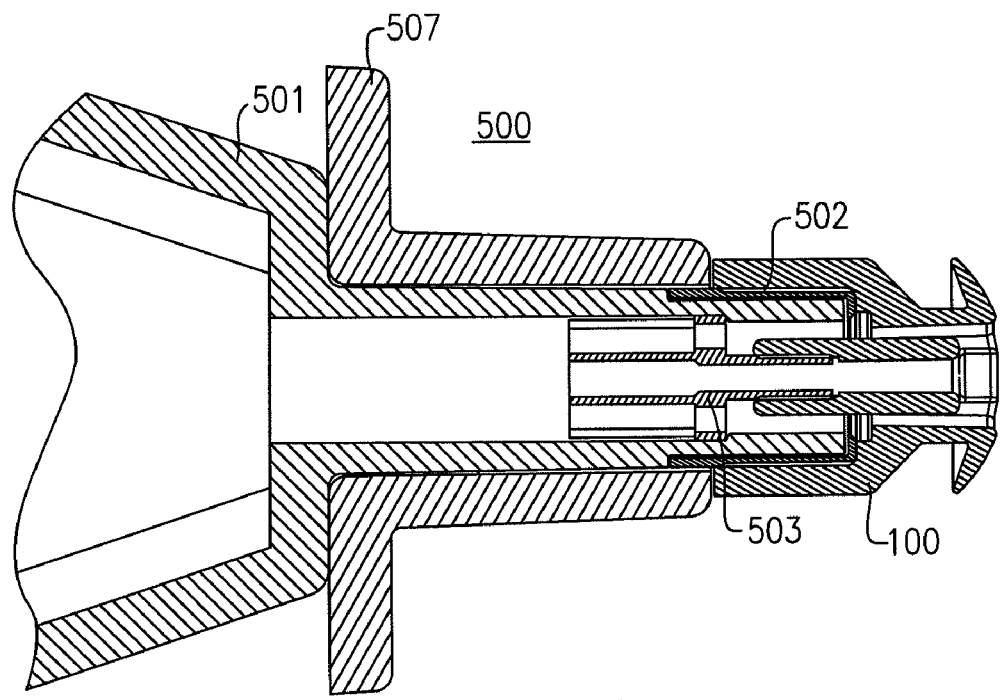
FIG. 5A shows an illustration of the tip of FIG. 4A and FIG. 4B inserted onto the front end of a medical instrument.

Turning now to FIG. 5A, an exemplary tip 100 is shown as affixed to an exemplary medical instrument, such as a tympanometric instrument, where the tip 100 provides an acoustic as well as a pneumatic interface with a human ear. FIG. 5A shows a simplified cutaway side view of the instrument front end 500 and tip 100. Exemplary medical instrument front end 500 includes a reinforcing sleeve 502 and a central core 503. A tip ejector 507 can be provided, this component being configured to slide axially to eject tip 100, such as after use or for changing to another sized tip. In some embodiments, tip ejector 507 can be manually operated by pushing tip ejector 507 laterally towards tip 100, thus sliding tip 100 off of both reinforcing sleeve 502 and central core 503.

Figure 5B:
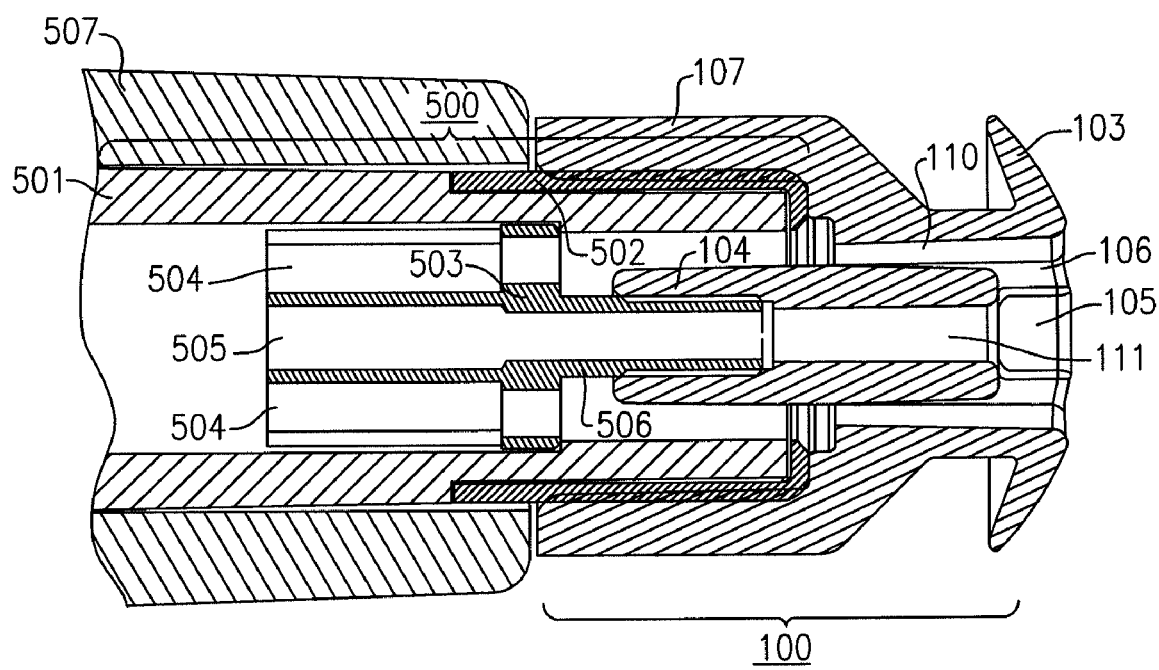
FIG. 5B shows a slightly more detailed cutaway side view of one exemplary front end and tip of FIG. 5A.

Reinforcing sleeve 502 can be disposed on housing 501 to provide a stiffer or more resilient material in order to reduce wear caused by sliding tips 100 on and off of the front end 500 and/or to provide a better pneumatic seal with a tip 100. Reinforcing sleeve 502 and a portion of body 501 under reinforcing sleeve 502 can substantially fill the cylindrical volume between an inner surface of tip section 107 and an outer surface of tip section 104. Reinforcing sleeve 502 also can provide protection for central core 503 disposed within a medical instrument housing 501, particularly for the stem section 506 of central core 503 (FIG. 5B) which might otherwise be exposed to potential impact damage when a removable tip 100 is not present. Now turning to FIG. 5B, note that the stem section 506 of central core 503, a continuation of the microphone tube (a microphone extension tube), extends into section 104 of tip 100 by slidable engagement, and thus substantially isolates the microphone channel from the speaker and pressure channels 110 until opening 105. Note that the overlapping nature the engagement between section 104 of tip 100 and the stem section 506 of central core 503 is configured such that a user does not have to place the tip onto the front end with precision. Once a small amount of engagement has occurred, the central channel stays isolated from the other components, and the threat of Helmholtz resonating is eliminated. As shown in the natural stopped position of FIG. 5B, a tip 100 already has more than sufficient overlap, even if not slid all of the way onto reinforcing sleeve 502. Thus a user not paying full attention to tip placement can still obtain accurate measurements, despite an imprecise positioning (i.e. a tip not seated all of the way to the natural stop).

In terms of materials, the housing 501 can typically be manufactured from a plastic-type material that can be formed, such as for example, by injection molding, or other similar process. Reinforcing sleeve 502 can be manufactured from any substantially rigid material, such as plastic or metal, including brass, stainless steel, or aluminum. Central core 503 can be cast or otherwise manufactured from any substantially suitable rigid materials, such as plastics or metals including brass, stainless steel, or aluminum. The specific types of materials used to manufacture housing 501, reinforcing sleeve 502, and central core 503 are not essential to the workings of these components and are intended to be exemplary for the sake of completeness.

Figure 6A:
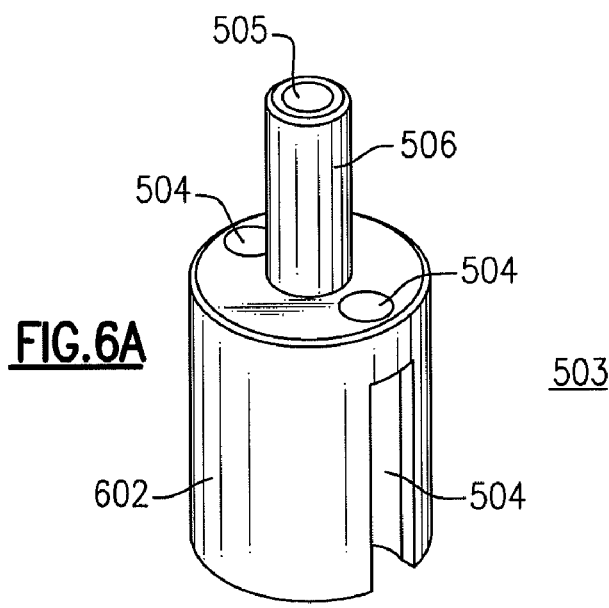
FIG. 6A shows a perspective view of an exemplary central core of a tip including a stem section.
Figure 6B:
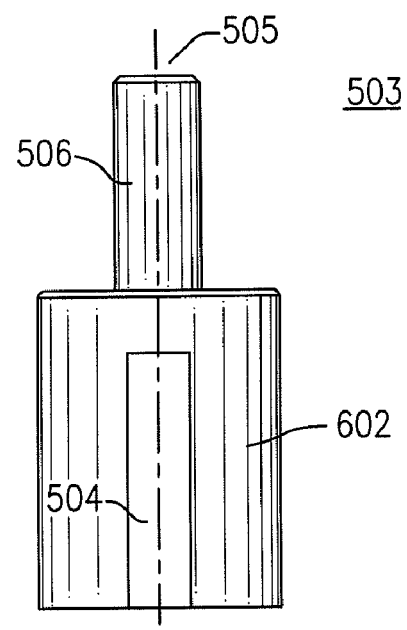
FIG. 6B shows a side view of the exemplary central core of FIG. 6A.
Figure 6C:
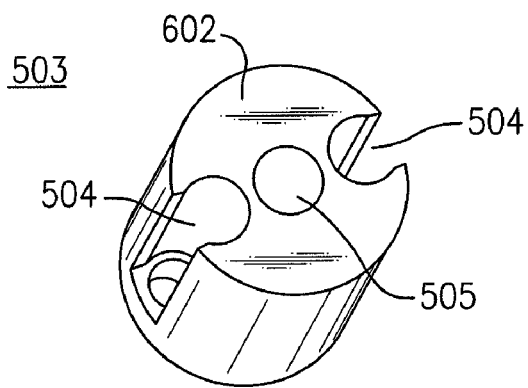
FIG. 6C shows another perspective view of an exemplary central core highlighting the lower section.

FIG. 6A shows a perspective view of an exemplary central core 503, including a stem section 506. Referring now FIG. 5B in addition to FIG. 6A, a lower section 602 of central core 503 includes a set of channels 504 which extend the speaker and pressure channels 110 from tip 100 openings 106 as well as extending the microphone channel 505 from microphone channel 111 within tube 110 of tip 100 to tip 100 opening 105. Lower section 602 of central core 503 also supports stem section 506. Note that section 104 of tip 100 indexes onto stem section 506 when a removable tip 100 is affixed to the medical instrument front end section 500 (See also FIG. 5A). FIG. 6B shows a side view of an exemplary central core 503. FIG. 6C shows a perspective view of an exemplary central core 503 highlighting lower section 602.

As described further below, tips and associated mating components used on traditional 226 Hz tympanometric devices typically have acoustic characteristics that can reduce the accuracy of measurements made at 1,000 Hz or higher frequencies. Also, prior art devices generally use tips that require accurate physical placement to maintain measurement accuracy as well as using front end construction that contains fragile components.

Many prior art front ends also have the undesirable characteristic that cerumen (i.e. ear wax) or other debris can clog them and thereby compromise the resulting impedance or admittance data. Tips as described herein are more robust, more reliable, and user friendly with regard to tip placement. The typically pliable nature of most tip seals as construed herein can provide some cushioning to help protect typically more fragile front end components.

Figure 7A:
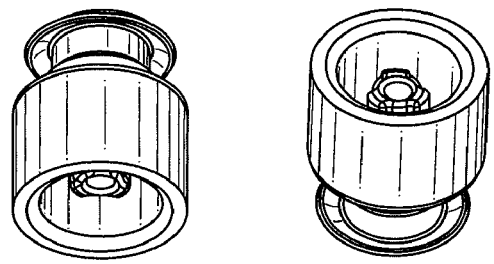
FIG. 7A shows an exemplary (neo-natal) sized tip according to the invention.
Figure 7B:
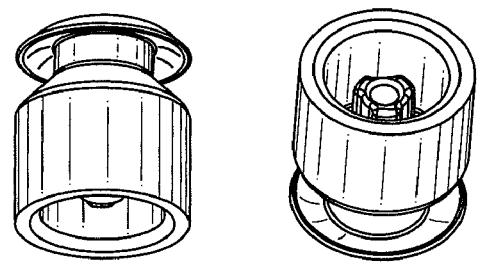
FIG. 7B shows an exemplary small sized tip according to the invention.
Figure 7C:
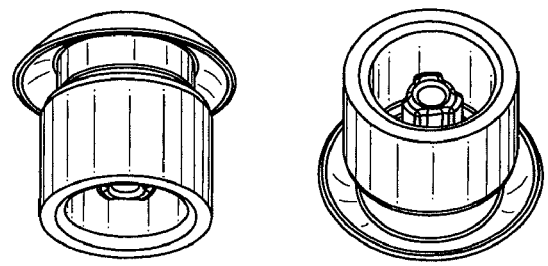
FIG. 7C shows an exemplary medium sized tip according to the invention.
Figure 7D:
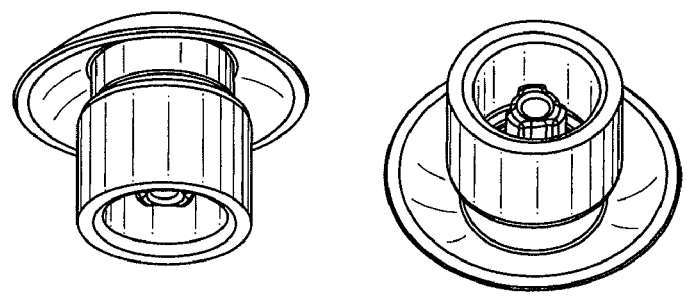
FIG. 7D shows an exemplary large sized tip according to the invention.
Figure 7E:
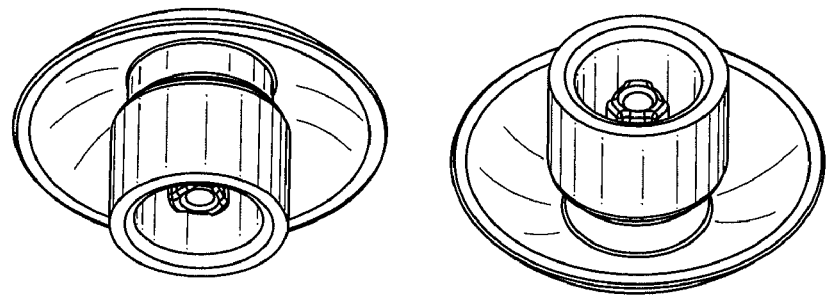
FIG. 7E shows an exemplary extra large sized tip according to the invention.

It will be readily apparent that a plurality of various sized tips 100 can be made available in order to fit most typical human ear shapes and sizes. Typical sizes include neo (neonatal) (FIG. 7A), small (FIG. 7B), medium (FIG. 7C), adult large (FIG. 7D), and adult extra large tips (FIG. 7E). Generally the size and/or shape of the distal sealing surface 103 changes while tip sections 104 and 107 remain substantially constant so as to provide a standard connection to the front end of a medical instrument.

According to this description, the central pathway including stem 506 and channel 505 generally connects with the microphone. However, it should be noted that the microphone and speaker can be switched since isolation between the two pathways is maintained as long as at least one channel ends substantially at the distal end of the tip. While a microphone acoustic path and speaker acoustic path have been designated according to the exemplary embodiments, the specific path or paths used for the microphone and the speaker are not essential and as noted above, and can be switched. For example, the isolated acoustic paths, e.g. opening 105, shown substantially in the center of the distal sealing surface 103 and air channel 111, and the openings 106 and air channels 110 of FIG. 1A and FIG. 2B need not be assigned to the microphone acoustic path or the speaker acoustic path.

Since the acoustic channels are interchangeable as to function, regarding the exemplary embodiments described above, reference is herein made to opening 105, shown substantially in the center of sealing surface 103 and air channel 111, as a "first acoustic path", and to the openings 106 and air channels 110 as a "second acoustic path". More generally, a first acoustic path includes an acoustic tube acoustically coupled to at least one of a plurality of openings in the tip seal, where the acoustic tube can be disposed within the tip. A second acoustic path can be acoustically coupled to at least another one of the plurality of openings in the seal. At least one of the first acoustic path and the second acoustic path can be configured for acoustic transmission. Another path, (first acoustic path or second acoustic path) can be configured for acoustic detection. The acoustic tube of the first acoustic path can be configured to substantially acoustically isolate the first acoustic path from the second acoustic path and thereby substantially suppresses Helmholtz resonance effects at the tip.

There are prior art tips and front end assemblies in existence for operation at 1,000 Hz. Typically such prior art tips and front end assemblies have small, delicate tubes without sufficient mechanical protection. Such prior art tubes typically can also act as sharp surfaces that can scrape off ear wax and therefore tend to plug more easily with ear wax. Small, sharp components can also potentially injure a patient. By contrast, the herein described tip presents only relatively smooth surfaces to the surfaces of the ear under examination.

Figure 8A:
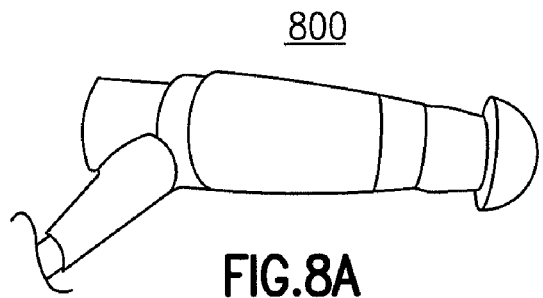
FIG. 8A shows a side view of a prior art probe using a single bore tip.
Figure 8B:
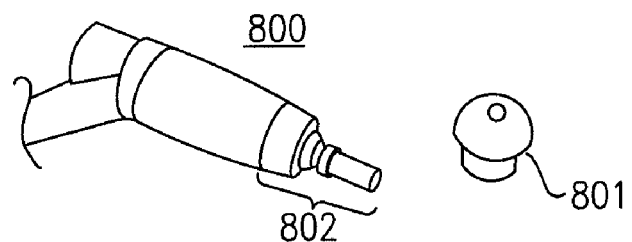
FIG. 8B shows a side view of the probe of FIG. 8A with the single bore tip removed.

Another problem with prior art tips that can operate at 1,000 Hz is that most are single bore tip types similar to the type of prior art tip shown in FIG. 1. For example, FIG. 8A shows a side view of a prior art probe 800 for use at 1,000 Hz. FIG. 8B shows a side view of the probe front end 802 of FIG.

Figure 8C:
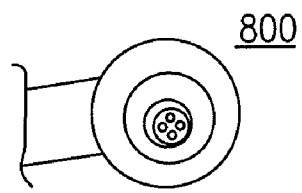
FIG. 8C shows an end view of the acoustic channels of the probe front end.
Figure 8D:
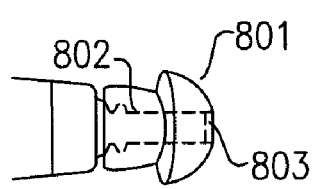
FIG. 8D illustrates how a slightly misplacement of the prior art tip of FIG. 8B can create a volume that causes undesired Helmholtz resonation.
Figure 8E:
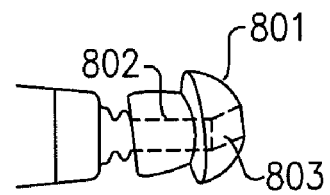
FIG. 8E, illustrates how a slightly different misplacement of the prior art tip as shown in FIG. 8D can also create a volume that causes undesired Helmholtz resonation.

8A with the single bore prior tip 801 removed. FIG. 8C shows an end view of the acoustic channels of the probe front end 802. One problem with this prior tip design is that it only works properly when tip 801 is completely and properly seated on the probe front end 802. As shown in FIG. 8D and FIG. 8E, the slightest improper placement of a tip 801 causes the formation of an unintended volume or cavity 803. With only a slight error in mounting tip 801, the unintended cavity 803 can cause undesirable Helmholtz resonation with such a prior art probe 800. Misplacement of removable parts such as removable tips 801 on medical instruments have been found to be relatively common, especially in non-specialized uses as in front line office and high volume family practice or pediatric settings. Misplacement (misalignment) of a tip can also occur routinely in harsh field environments or where clinicians are rushed, such as in typical hospital ER settings where clinicians have little time to make diagnostic measurements.

By contrast, as discussed above in regard to FIG. 5A and FIG. 5B, a tip 100 according to the invention, for example, when used with an exemplary front end 500, need only make a substantially air tight connection at reinforcing sleeve 502 and where tip 100 indexes onto a stem section 506. Even with a relatively poor placement (poor, but still sufficient mechanical overlap) of tip 100, Helmholtz resonation does not occur because acoustic tube 101 continues as a separate tube substantially out to the distal end of tip 100. Also note that acoustic tube 101 can be typically provided coaxially substantially on a longitudinal axis of tip 100. Therefore, since there is substantial axial symmetry (axissymmetry), a tip 100 having a substantially centered acoustic tube 100 can also be rotated about the longitudinal axis without causing measurement error. Also, because of the flexibility of rotation and range of slidable mechanical engagement, there is no need for orienting features, such as for example, but not limited to, mechanical detents, rims, angled rims, or slots.

Thus, it can be seen that the tip remains substantially free of Helmholtz resonance over a range of slidable mechanical engagement (range of overlap). Also, where there is insufficient indexing of a tip 100 onto a stem section 506, an inventive tip 100 most likely would give no useable measurement, as opposed to an erroneous measurement. Thus, a medical instrument using the inventive tip is far more likely to yield repeatable and accurate measurements.

Laboratory Tip Testing and Helmholtz Resonance:

When a tone at a specified decibel (dB) level is played into a cavity, i.e. the ear canal, for accurate medical testing, a microphone listening to the sound reflected from the cavity should report back an accurate decibel level. If, however, Helmholtz resonation starts, the microphone can indicate a lower sound level than actually exists. In the laboratory tests of the following examples, we maintained a known, constant dB level. Therefore, for any given cavity size, and in the absence of Helmholtz resonance, the resulting plots should substantially match each other. However, as demonstrated in laboratory testing, for prior art 226 Hz tips, while at 226 Hz the two plots follow each other closely, the two plots began to separate significantly as the frequency was increased.

Figure 9A:
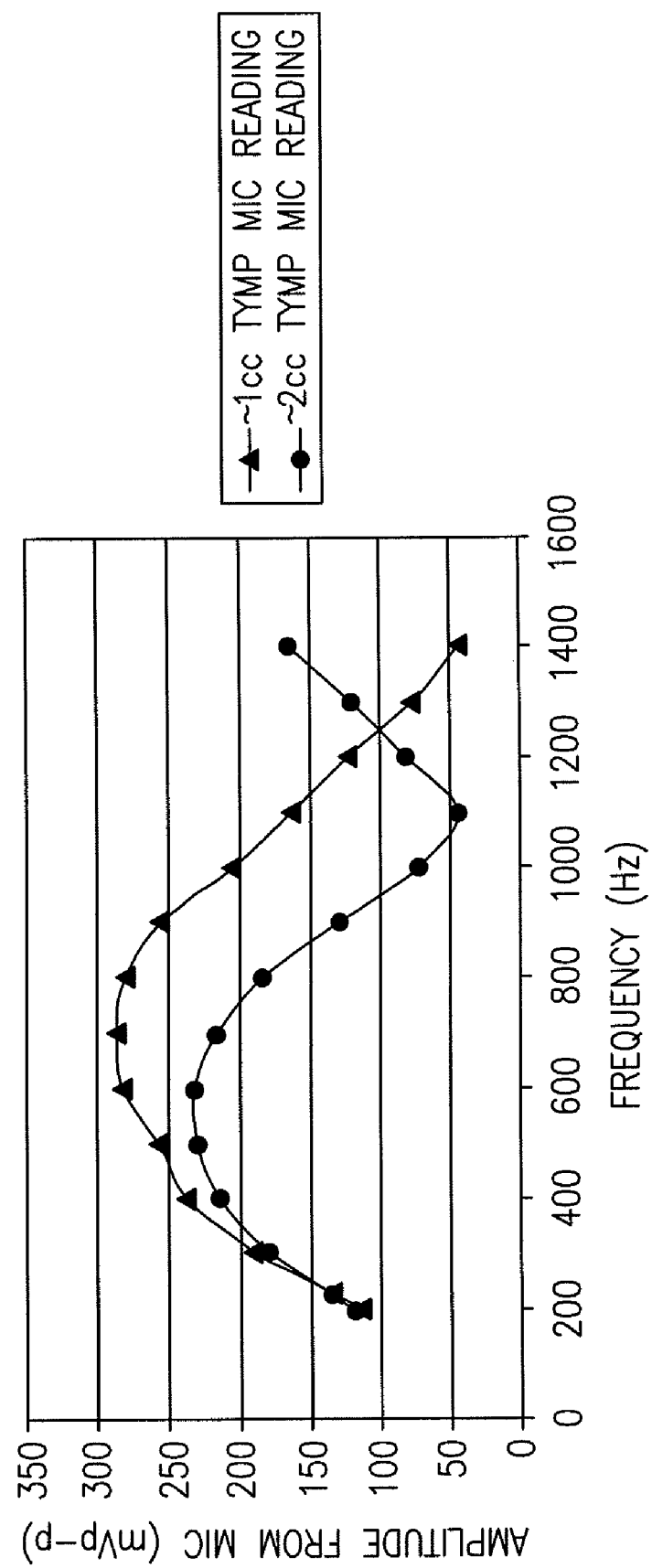
FIG. 9A shows a graph of sound amplitude at a microphone recorded as a microphone voltage output in millivolts (peak to peak (mV p-p) plotted against frequency for a prior art, traditional 226 Hz device tip.

Example: FIG. 9A shows a graph of sound amplitude at a microphone recorded as microphone voltage output in millivolts (peak to peak (mV p-p) plotted against frequency for a prior art tip. The triangular shaped points were recorded for a simulated 1 cc volume and the circular data points taken for a simulated 2 cc volume. The graph of FIG. 9A was generated using a tympanometric instrument attached to a B&K type 4946 2 cc microphone coupler. A volume reducing sleeve was affixed into the B&K coupler to simulate the smaller 1 cc volume. A calibrated B&K ½" type 4192 microphone was attached to the other side of the coupler. A test setup using LabView software (available from National Instruments of Austin, Tex.) was used to drive the tympanometric instrument's speaker until the Calibrated B&K microphone measured 85 dB sound pressure level (SPL). Once 85 dB was reached the response from the tympanometric instrument's microphone was recorded (mV p-p). This was repeated across a range of frequencies in the 200-1400 Hz range for both the 1 cc and 2 cc simulated volumes. As can be seen in FIG. 9A (a prior art tip), although the sound pressure level was maintained at 85 dB for each frequency, the tympanometric instrument's microphone reported a significantly different response for the two cavity sizes. Note that the difference between the two curves of FIG. 9A increases with frequency. While illustrating a substantially similar and proper response at about 226 Hz, the difference between the two curves at 1,000 Hz would present a relatively a large instrument error were such a prior art tip used at the higher frequency. By contrast, FIG. 9B shows a graph of the results of the same laboratory test performed using a tip having a microphone tube, such as the exemplary acoustic tube 101 of FIG. 2A. FIG. 9B shows a substantially consistent response more consistent across the 1 cc and 2 cc test volumes. According to our best present understanding of the operation of the inventive tip, we attribute the significantly improved response to suppression of Helmholtz resonance at the tip caused by the isolation provided by the microphone tube added to the presently described tip design. Further, the tube can interface with the ear canal substantially at the extreme distal end of the device.

Tympanometry

It is anticipated that one application of the tip design described herein will be for use with a tympanometric instrument, a medical instrument that can measure various acoustic-physiological parameters of the human ear. Acoustic admittance, a parameter measured by a tympanometric instrument, is the ease with which acoustic energy is transferred from one system to another. If the air in the ear canal is easily set into vibration, the admittance is high. If the air is difficult to set into vibration, the admittance of the system is low. The ease or difficulty of setting the air in the ear canal into vibration is determined by the volume of air and the admittance of the middle ear. Tympanometry provides a method of evaluating the physical characteristics of the ear canal/middle ear system by measuring the admittance of the air trapped in the ear canal. Tympanometry includes the measurement of acoustic admittance as a function of ear canal air pressure. The resulting graph is a tympanogram. Because ear canal air pressure changes the admittance of the tympanic membrane and middle ear, the admittance reported by the tympanometric instrument changes when the ear is pressurized. Positive or negative pressure, introduced into the sealed ear canal, decreases the admittance of the air in the ear canal by stiffening the eardrum. The effect of air pressure on the acoustic admittance measured in the ear canal is systematically altered by ear disease. Tympanometry is a sensitive indicator of the effects of ear disease on the acoustical and mechanical function of the middle ear.

Figure 10A:
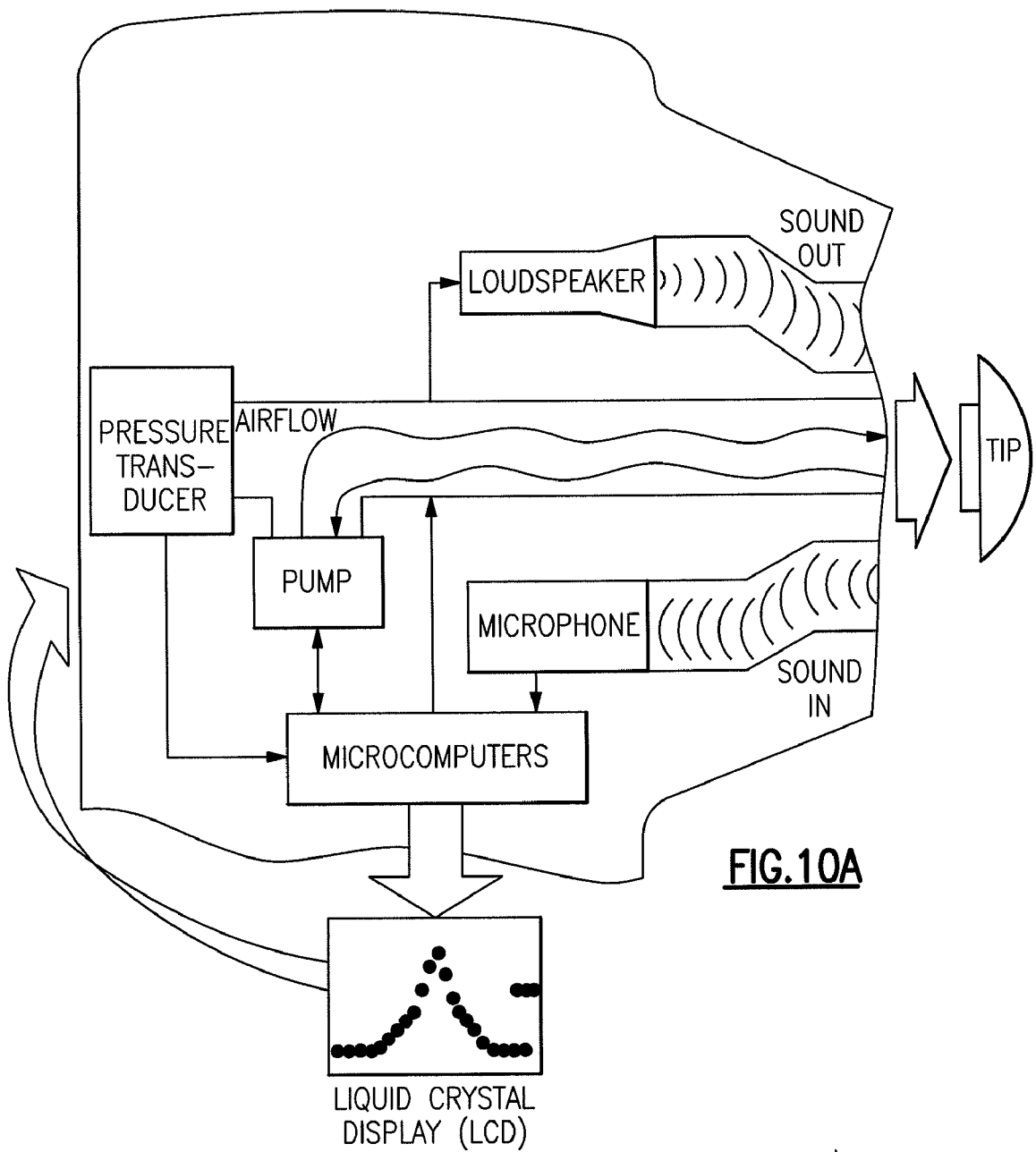
FIG. 10A shows a block diagram of an exemplary tympanometric instrument suitable for use with the inventive tip.
Figure 10B:
FIG. 10B illustrates the tympanometric instrument of FIG. 10A as positioned on a patient's ear.

A block diagram of one exemplary tympanometric instrument is illustrated in FIG. 10A. As shown by FIG. 10B, a tone can be introduced into the sealed ear canal by a miniature loudspeaker. Prior art instruments and tips operate at 226 Hz by medical convention. A miniature microphone records and monitors the sound pressure produced in the ear canal. The sound level is typically maintained at a constant 85 dB SPL (Sound Pressure Level) throughout the test by a microcomputer. When the amount of sound absorbed by the middle ear increases, the speaker can be driven harder by increasing the drive voltage to maintain the constant SPL. The voltage required to maintain the probe tone at 85 dB SPL is proportional to the acoustic admittance of the ear. Air pressure in the ear canal can be changed with a miniature pump. The pressure transducer monitors air pressure, feeding this information to another microcomputer so that it can control the rate of pressure change (sweep rate). As pressure in the ear canal is changed throughout a test, a microcomputer computes acoustic admittance and plots admittance as a function of pressure on the liquid crystal display. As indicated by the errors shown by the curves in the graph of FIG. 9A, a tip according to the prior art can give satisfactory results for traditional tympanometric instrument operation at 226 Hz. However, it is anticipated that at higher frequencies, such an instrument cannot yield accurate measurements for the range of volumes expected for the human ear anatomy using the prior art tip designs. A tympanometric instrument operating at higher frequencies, such as 1,000 Hz, can however, yield substantially accurate results using a tip according to the present invention.

It can now be seen that the inventive tip is suitable for operation at traditional frequencies from 200 Hz (including 226 Hz) as well as at 300 Hz and above, including the newly proposed standard frequency of 1,000 Hz.

While the acoustic tube has been shown in an exemplary embodiment as coupled to a single opening substantially in the center of the seal, an acoustic tube can alternatively be coupled to one or more opening not at the center of seal.

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

While the present invention has been particularly shown and described with reference to the preferred mode as illustrated in the drawing, it will be understood by one skilled in the art that various changes in detail may be affected therein without departing from the spirit and scope of the invention as defined by the claims.

APPENDIX I

Figure 11:
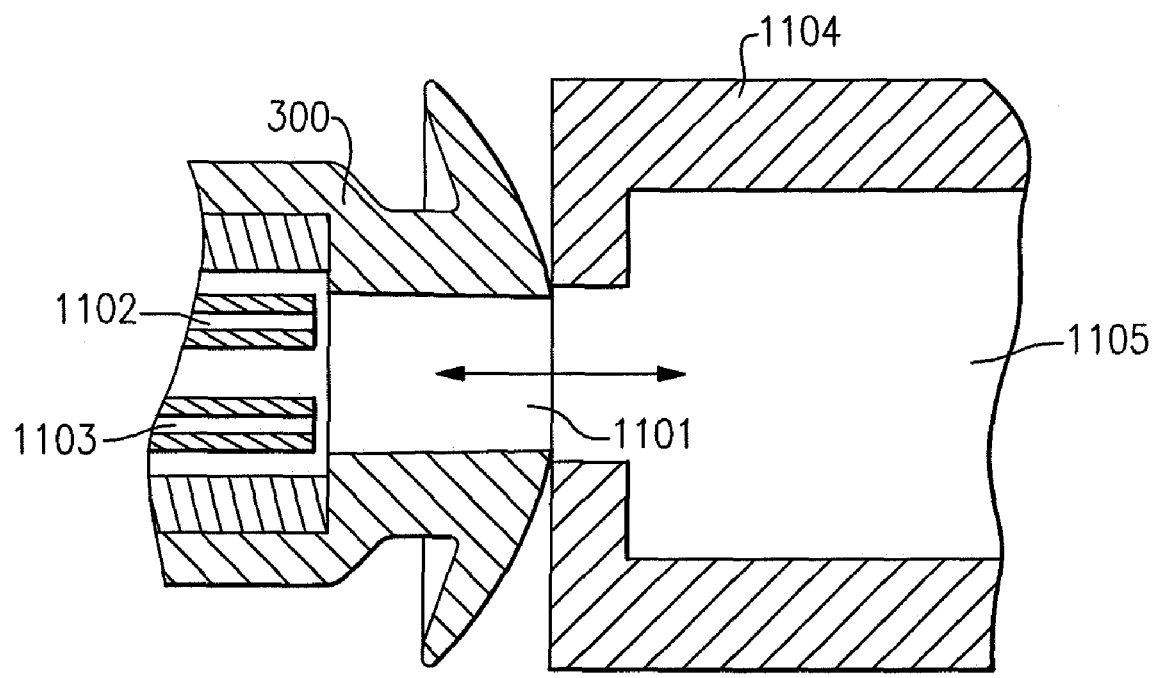
FIG. 11 shows a conceptual diagram of a tip according to the prior art sealed against a test cavity volume.

The Helmholtz acoustic phenomenon is now described in more detail. FIG. 11 shows a conceptual diagram of a tip 300 according to the prior art sealed against a test cavity volume. The test cavity volume 1105 represents an ear canal. In the exemplary system of FIG. 11, acoustic tube 1102 is used to generate a test sound pressure at a tone of frequency f, such as by use of a speaker driving acoustic tube 1102 (not shown in FIG. 11). Acoustic tube 1103 is used for detection with an acoustic detector (not shown in FIG. 11), such as a microphone.

A region of air resides between the acoustic tubes 1102 and 1103 and the larger test cavity volume 115. Under certain conditions, the sound that issues from acoustic tube 1102 can cause a slug of air 1101 to begin to move as a unit into the larger volume 1105, which in turn acts a spring element and bounces slug of air 1101 back. The slug 1101 can oscillate between two positions at some resonant frequency, much as a classic mass and spring system does. When the slug 1101 moves as a unit, however, the air around the acoustic tubes experiences a slight density change and a corresponding sound pressure level change. Thus the sound detection tube (here, acoustic tube 1103) senses a pressure level smaller in magnitude than the actual sound pressure level in the larger volume.

When the slug of air has a cylindrical shape, equation 1 can be used to predict the resonance frequency:

$$f = \frac{c}{2\pi}\sqrt{\frac{A}{VL}}$$

Where f=resonance frequency, c=speed of sound, A=cross sectional area of the air slug, V=volume of air in the ear canal or similar cavity, and L=length of air slug. The situation of reduced detected sound level can occur when a tone (frequency f) is produced that matches within some range of the conditions as defined by equation 1.

We claim:

1. A tip for coupling sound between a medical instrument and an ear comprising:
    a sealing surface configured to substantially conform said tip to an auditory canal of the ear, said sealing surface including a plurality of openings;
    a first acoustic path comprising an acoustic tube acoustically coupled to at least one of said plurality of openings, said acoustic tube being disposed within said tip; and
    a second acoustic path acoustically coupled to at least another one of said plurality of openings in said sealing surface,
    wherein a selected one of said first acoustic path and said second acoustic path is configured for acoustic transmission, and another one of said first acoustic path and said second acoustic path is configured for acoustic detection, said acoustic tube of said first acoustic path being configured to substantially acoustically isolate said first acoustic path from said second acoustic path,
    wherein said tip remains substantially free of Helmholtz resonance over a range of slidable mechanical engagement, and
    wherein a center of said acoustic tube is mechanically suspended substantially coaxially on a longitudinal axis of said tip.

2. The tip of claim 1, wherein said tip comprises one or more mechanical attachment members configured to mechanically suspend said acoustic tube within said tip.

3. The tip of claim 2, wherein said acoustic tube and said one or more mechanical attachment members comprise substantially the same material.

4. The tip of claim 3, wherein said material comprises a pliable material.

5. The tip of claim 4, wherein said pliable material comprises a silicone.

6. The tip of claim 1, wherein said a sealing surface comprises a diameter larger than an opening to said auditory canal.

7. The tip of claim 1, wherein said configuration to substantially acoustically isolate said first acoustic path from said second acoustic path reduces noise.

8. The tip of claim 1, wherein said configuration to substantially acoustically isolate said first acoustic path from said second acoustic path provides artifact rejection.

9. The tip of claim 1, wherein at least a selected one of said first acoustic path and said second acoustic path is acoustically coupled to an acoustic detector configured for said acoustic detection.

10. The tip of claim 9, wherein said acoustic detector comprises a microphone.

11. The tip of claim 1, wherein said acoustic path is configured for acoustic transmission comprises at least one speaker.

12. The tip of claim 1, further comprising a plurality of acoustic paths, at least a selected one of said plurality of acoustic paths acoustically coupled to more than one of said plurality of openings.

13. The tip of claim 1, wherein said acoustic path configured for acoustic transmission operates at one or more selected frequencies over a range of frequency of about 200 Hz to 20 kHz.

14. The tip of claim 13, wherein said acoustic transmitter operates at about 1,000 Hz.

15. The tip of claim 1, wherein said tip is a disposable tip.

16. The tip of claim 15, wherein said tip is configured for single use and wherein at least said sealing surface comprises a material designed to deteriorate to discourage reuse.

17. The tip of claim 16, wherein at least a portion of said tip is configured to deteriorate on exposure to a cleaning chemical.

18. The tip of claim 1, wherein said medical instrument comprises a tympanometric instrument.

19. The tip of claim 18, wherein said tympanometric instrument further comprises at least one pump configured to apply a pressure in said auditory canal via said at least one at least one of said plurality of openings in said sealing surface.

20. An acoustic measurement apparatus comprising:
   a tip including a sealing surface configured to substantially conform said tip to an auditory canal of the ear, said sealing surface including a plurality of openings, said tip further comprising an acoustic tube acoustically coupled to at least one of said plurality of openings defining a first acoustic path, said acoustic tube being disposed within said tip, said tip also including a second acoustic path acoustically coupled to at least another one of said plurality of openings in said sealing surface,
   wherein a selected one of said first acoustic path and said second acoustic path is configured as a path for acoustic transmission, and another one of said first acoustic path and said second acoustic path is configured as a path for acoustic detection, and said acoustic tube of said first acoustic path is configured to substantially acoustically isolate said first acoustic path from said second acoustic path;
   an acoustic measuring device, said acoustic measuring device comprising:
   a front end which receives said tip, said front end including at least two acoustic paths configured to acoustically couple to said first acoustic path and said second acoustic path of said tip,
   wherein said tip remains substantially free of Helmholtz resonance over a range of slidable mechanical engagement, and
   wherein a center of said acoustic tube is mechanically suspended substantially coaxially on a longitudinal axis of said tip;
   an acoustic transmitter acoustically coupled via said path for acoustic transmission;
   an acoustic detector coupled via said path for acoustic detection; and
   an electronics package electrically coupled to said acoustic transmitter, said electronics package also electrically coupled to said acoustic detector, said electronics package including at least one microcomputer, said at least one microcomputer configured to run an algorithm for performing an acoustic measurement.

21. The tip of claim 20, wherein said tip comprises one or more mechanical attachment members configured to mechanically suspend said acoustic tube within said tip.

22. The tip of claim 21, wherein said tip, including said acoustic tube and said one or more mechanical attachment members comprise substantially the same material.

23. The tip of claim 22, wherein said material comprises a pliable material.

24. The tip of claim 23, wherein said pliable material comprises a silicone.

25. The tip of claim 20, wherein said sealing surface comprises a diameter larger than an opening to said auditory canal.

26. The tip of claim 20, wherein said configuration to substantially acoustically isolate said first acoustic path from said second acoustic path reduces noise.

27. The tip of claim 20, wherein said configuration to substantially acoustically isolate said first acoustic path from said second acoustic path provides artifact rejection.

28. The tip of claim 27, wherein said acoustic detector comprises a microphone.

29. The tip of claim 20, wherein said acoustic path is configured for acoustic transmission comprises at least one speaker.

30. The tip of claim 20, further comprising a plurality of acoustic paths, at least a selected one of said plurality of acoustic paths acoustically coupled to more than one of said plurality of openings.

31. The tip of claim 20, wherein said acoustic path configured for acoustic transmission operates at one or more selected frequencies over a range of frequency of about 200 Hz to 20 kHz.

32. The tip of claim 31, wherein said acoustic transmitter operates at about 1,000 Hz.

33. The tip of claim 20, wherein said tip is a disposable tip.

34. The tip of claim 33, wherein said tip is configured for single use and wherein at least said sealing surface comprises a material designed to deteriorate to discourage reuse.

35. The tip of claim 34, wherein at least a portion of said tip is configured to deteriorate on exposure to a cleaning chemical.

36. The tip of claim 20, wherein said medical instrument comprises a tympanometric instrument.

37. The tip of claim 20, wherein said tympanometric instrument further comprises at least one pump configured to apply a pressure in said auditory canal via said at least one at least one of said plurality of openings in said sealing surface.

38. The acoustic measurement apparatus of claim 20, wherein said apparatus is a portable instrument further comprising a display communicatively coupled to said microcomputer and configured to display a result of a tympanometric measurement.

39. The acoustic measurement apparatus of claim 20, wherein said front end further comprises a central core including a central core stem section, and said central core stem section is configured to slidably engage said acoustic tube to complete said first acoustic path.

40. The acoustic measurement apparatus of claim 39, wherein said central core further includes at least one acoustic channel acoustically coupled to said second acoustic path of said tip.

41. The acoustic measurement apparatus of claim 39, wherein said front end further comprises a reinforcing sleeve disposed coaxially over said central core and said reinforcing sleeve is configured to mechanically engage said tip to mechanically mount said tip onto said front end.

42. A method of affixing a tip for the acoustic measurement of an ear to a front end of an acoustic measurement instrument comprising the steps of:
  (a) providing an acoustic tip configured to make a seal with an auditory canal of the ear, said sealing surface including a plurality of openings, and defining at least a first and a second acoustic path, said first acoustic path of said tip including an acoustic tube substantially extending substantially to said sealing surface;
  (b) providing an acoustic instrument front end configured to mate to said tip,
  wherein said tip remains substantially free of Helmholtz resonance over a range of slidable mechanical engagement, and
  wherein a center of said acoustic tube is mechanically suspended substantially coaxially on a longitudinal axis of said tip; and
  (c) sliding said tip onto said front end to sealingly engage both said acoustic tube of said at least a first acoustic path and said second acoustic path of said tip with at least a first and a second acoustic path of said front end.

43. The method of claim 42, further comprising the step (d) sliding said tip off of said front end to sealingly dis-engage both said acoustic tube of said at least a first acoustic path and said second acoustic path of said tip using an ejector device.

* * * * *